United States Patent [19]

Berthe et al.

[11] Patent Number: 5,332,836

[45] Date of Patent: Jul. 26, 1994

[54] ACRYLATES, CONTAINING AN ALCOHOL, ALDEHYDE AND/OR ETHER FUNCTIONAL GROUP, PROCESS FOR THEIR MANUFACTURE AND THEIR APPLICATION TO THE PRODUCTION OF NEW POLYMERS AND COPOLYMERS

[75] Inventors: Marie-Christine Berthe; Paul Caubere; Yves Fort, all of Vandoeuvre les Nancy, France

[73] Assignee: Atochem, Paris, France

[21] Appl. No.: 22,226

[22] Filed: Feb. 25, 1993

Related U.S. Application Data

[62] Division of Ser. No. 721,751, Jun. 27, 1991, Pat. No. 5,206,389.

[30] Foreign Application Priority Data

Jun. 27, 1990 [FR] France .................. 90 08108

[51] Int. Cl.$^5$ ............... C07D 313/00; C07D 307/78; C07D 307/02
[52] U.S. Cl. .................. 549/346; 549/420; 549/475; 549/510; 549/466
[58] Field of Search ............... 549/420, 466, 346, 475, 549/510

Primary Examiner—C. Warren Ivy
Assistant Examiner—A. A. Owens
Attorney, Agent, or Firm—Millen, White, Zelano & Branigan

[57] ABSTRACT

Acrylates of the formula

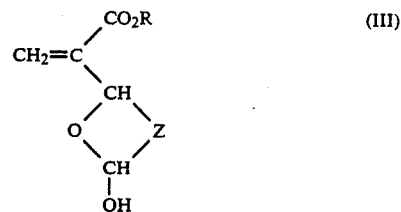

in which:
R is a radical chosen from alkyl radicals containing from 1 to 12 carbon atoms, cycloalkyl radicals containing from 5 to 12 carbon atoms, and aryl, arylalkyl and alkylaryl radicals,
Z is a hydrocarbon radical containing at least two carbon atoms forming with the oxygen and the two adjacent carbons a ring containing from 4 to 8 members.

8 Claims, No Drawings

ACRYLATES, CONTAINING AN ALCOHOL, ALDEHYDE AND/OR ETHER FUNCTIONAL GROUP, PROCESS FOR THEIR MANUFACTURE AND THEIR APPLICATION TO THE PRODUCTION OF NEW POLYMERS AND COPOLYMERS

This is a division, of application Ser. No. 07/721,751 filed Jun. 27, 1991 now U.S. Pat. No. 5,206,389.

BACKGROUND OF THE INVENTION

The present invention relates to new acrylates carrying at least two functional groups chosen from the alcohol, aldehyde and ether functional groups, to a process for their manufacture and to the production of new polymers and copolymers from the said acrylates.

U.S. Pat. No. 3,743,669 discloses a process for the preparation of acrylic compounds of formula

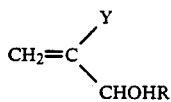

by reaction in a liquid phase at a temperature approximately from 0° to 200° C. of an α,β-olefinically unsaturated carboxylic acid derivative of formula $CH_2=CHY$ with an aldehyde of formula $RCHO$, Y being chosen from

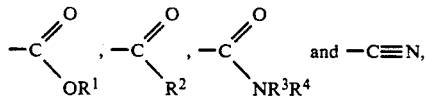

each of $R^1$ to $R^4$ denoting an alkyl ($C_1$-$C_{12}$), cycloalkyl ($C_5$-$C_{12}$), aryl, aralkyl or alkaryl, and R denoting alkyl ($C_1$-$C_8$), alk-($C_1$-$C_4$)aryl, aralkyl ($C_1$-$C_4$) or aryl, the said reaction being carried out in the presence of a catalytic quantity of a cyclic tertiary amine containing at least one nitrogen atom common to three rings. This reaction is very slow at room temperature. Thus, the reaction of 7.9 moles of acetaldehyde and 5.27 moles of ethyl acrylate at room temperature in the presence of 0.26 moles of diazabicyclo[2,2,2]-octane produces 93% of ethyl 2-(1-hydroxyethyl)acrylate only after 7 days. The same reaction carried out at 120°-124° C. takes place with a conversion of 82% at the end of 8 hours, but at the expense of selectivity. Furthermore, the Assignee Company has found that this reaction does not occur, even after 10 days, with some aldehydes whose carbonyl group is sterically hindered, such as trimethylacetaldehyde.

Bearing in mind the special behaviour which may be expected of acrylates containing a hydroxyl group in their structure, the Assignee Company has been concerned with obtaining new acrylates by functionalisation by means of dialdehydes.

SUMMARY OF THE INVENTION

A first subject of the present invention consists, therefore, of new acrylates chosen from those of formula

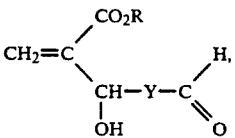

those of formula

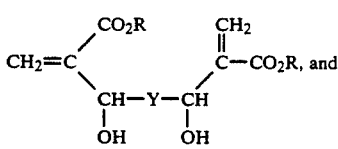

those of formula

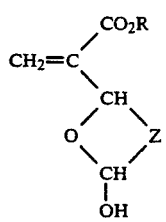

in which:

R is a radical chosen from alkyl radicals containing from 1 to 12 carbon atoms, cycloalkyl radicals containing from 5 to 12 carbon atoms, and atoll, arylalkyl and alkylaryl radicals, Y is a radical chosen from alkylene radicals containing from 1 to 12 carbon atoms, arylene radicals containing from 6 to 12 carbon atoms, heterocyclic radicals whose ring contains from 5 to 12 members and whose heteroatom is chosen from nitrogen, oxygen and sulphur, and alkylarylene radicals in which the alkyl part contains from 1 to 4 carbon atoms, and Y not being able to denote 1,4-phenylene when R denotes methyl, Z is a hydrocarbon radical containing at least two carbon atoms forming with the oxygen and the two adjacent carbons a ring containing from 4 to 8 members and preferably containing 5 or 6 members.

As examples of radicals R there may be mentioned especially the methyl, ethyl, n-propyl, isopropyl, n-butyl, isobutyl, phenyl and benzyl radicals. As examples of radicals Y there may be mentioned the radicals $(CH_2)_n$ in which n is an integer ranging from 4 to 12, phenylene (ortho, meta, para) radicals $C_6H_4$, 3,3'-diphenyl and 4,4'-diphenyl radicals, the 2,5-thiophenyl radical and 2,5-furyl radical.

As examples of radicals Z there may be mentioned especially the radicals $(CH_2)_2$ and $(CH_2)_3$ and the phenylene radical $C_6H_4$.

A second subject of the present invention consists of a process for the preparation of the acrylates of formulae (I) to (III). Although a common feature of the preparation of all these compounds is a stage involving an acrylate derived from an alcohol ROH and a diaidehyde, their synthesis nevertheless exhibits special features, depending on whether monoacrylates of formulae (I) and (III) or else diacrylates of formula (II) are involved. This is why the process of preparation according to the invention will now be described with reference to each of the classes of compounds according to the invention.

The preparation of the acrylates of formula (I) to (III) is carried out by reacting an acrylate of formula:

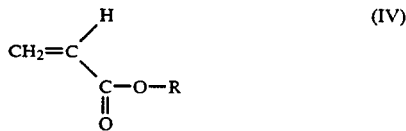

in which R is defined as above with a dialdehyde of formula

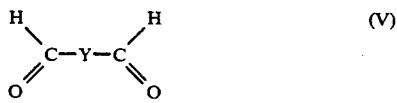

in which Y is defined as above, in the presence of an effective quantity of at least one functionalisation catalyst. As a functionalisation catalyst which is suitable for the reaction with an aldehyde there may be mentioned especially relatively strong bases such as cyclic tertiary amines containing at least one nitrogen atom common to three rings, described in U.S. Pat. No. 3,743,669, for example diazabicyclo[2,2,2]octane, quinuclidine and α-quinuclidinol. An effective quantity of functionalisation catalyst obviously depends on the nature of the latter, but also on the acrylate of formula (IV) and the aldehyde of formula (V). It is generally approximately between 2 and 20%, preferably approximately between 4 and 10 mol% relative to the sum of the reactants present—acrylate and dialdehyde.

As an example of dialdehydes of formula (V) there may be mentioned especially terephthalaldehyde, isophthalaldehyde, orthophthalaldehyde, glutaraldehyde, hexanedial, decanedial, dodecanedial, thiophene-2,5-dicarboxyaldehyde, furan-2,5-dicarboxaldehyde, 3,3'-biformyldiphenyl and 4,4'-biformyldiphenyl.

The process of preparation according to the invention can be additionally carried out in the presence of at least one electrophilic activator such as lithium chloride or fluoride in a quantity which may be up to approximately 5 mol% relative to the sum of the reactants present—acrylate and dialdehyde.

The process according to the invention may be additionally carried out in the presence of an organic solvent such as tetrahydrofuran, methylene chloride, chloroform, dioxane, acetonitrile, methyl ethyl ketone, ethanol, ethyl acetate and the like.

To make use of the process according to the invention a temperature of between 15° C. and 125° C. may be chosen, preferably approximately between 20° C. and 50° C., and not exceeding the boiling temperature of the solvent when a solvent is employed.

The reactants may be present in the reaction medium in any concentration. However, for reasons of kinetics it is generally preferable to avoid an excessively high dilution with the solvent and to conform to an acrylate/dialdehyde molar ratio of approximately between 0.2 and 10. The possible excess of one of the two reactants in relation to the other enables it then to act as a solvent.

Finally, the reaction according to the invention may be carried out in the presence of an effective quantity of at least one polymerisation inhibitor. As examples of polymerisation inhibitors which can be employed there may be mentioned especially phenothiazine, hydroquinone methyl ether, N,N-diethylhydroxylamine, nitrobenzene, di-tert-butylcatechol, hydroquinone, p-anilinophenol, di(2-ethylhexyl)octylphenyl phosphite, 2,5-di-tert-butyl-4-hydroxytoluene, methylene blue and their mixtures in all proportions. An effective quantity of polymerisation inhibitor is generally between 0.05% and 0-5% by weight of acrylic compound.

Although atmospheric pressure is generally satisfactory, the process according to the invention can also be used under pressure.

Depending on whether it is desired to direct the reaction according to the invention towards the production of monoacrylates of formulae (I) and (III) or else towards the production of diacrylates of formula (II), some special conditions must, nevertheless, be obeyed. In fact, the reaction according to the invention generally produces a mixture of a monoacrylate and of a diacrylate which must then, at a time chosen for stopping the reaction, be separated by a conventional separation technique. In some cases, the separation is facilitated by the difference in physical state between the two compounds formed, at normal pressure and temperature. Thus, for example, in the case of terephthalaldehyde, the monoacrylate formed is a liquid, whereas the diacrylate formed is a white solid. As already mentioned elsewhere, the monoacrylates of formula (III) are formed in preference to the monoacrylates of formula (I) when the dialdehyde of formula (V) which is employed for the reaction according to the invention is of a structure such that a cyclisation incorporating one of the oxygen atoms of the dialdehyde can easily take place. Such a possibility is particularly favourable when Y is a $(CH_2)_2$ or $(CH_2)_3$ radical or else a phenylene radical $C_5H_4$ on which the aldehyde functional groups are situated in the ortho position.

The composition of the mixture of monoacrylate and diacrylate which is formed by the reaction according to the invention is affected in a complex manner by a set of parameters such as:

the reaction time, it being possible for the latter to range from approximately 1 hour to approximately 12 days, depending on the reaction temperature and pressure which are chosen; the monoacrylate is generally formed first, in a virtually quantitative manner, after a relatively short time, of the order of a few hours at room temperature; in a second stage the monoacrylate disappears progressively, to form the diacrylate;

the nature of the solvent employed: all conditions being otherwise equal, the diacrylate is formed much more easily in tetrahydrofuran or methylene chloride than in chloroform;

the quantity of solvent employed: dilution with a solvent such as tetrahydrofuran slows down the first stage of formation of the monoacrylate and, to a still much greater extent, the second stage of formation of the diacrylate;

the quantity of functionalisation catalyst employed: all conditions being otherwise equal, an increase in the quantity of catalyst results in a slight acceleration of the monoacrylate formation stage and in a more pronounced acceleration of the diacrylate formation stage;

the acrylate/dialdehyde molar ratio: in the presence of solvent and at constant total volume, that is to say apart from the dilution effect, an increase in this ratio produces the acceleration of the diacrylate formation;

the reaction temperature: all conditions being otherwise equal, an increase in the temperature is reflected in a faster formation of the diacrylate.

The new acrylates according to the invention can polymerise or copolymerise with other ethylenically unsaturated monomers such as ethylene, as well as:

an alkyl acrylate or methacrylate in which the linear or branched alkyl group, optionally substituted, for example, with at least one halogen atom such as chlorine or fluorine and/or by at least one hydroxyl group, contains from 1 to 20 carbon atoms, an aryl acrylate or methacrylate such as benzyl methacrylate, a vinylaromatic hydrocarbon such as styrene, vinyltoluene, α-methylstyrene, 4-methylstyrene, 3-methylstytene, 4-methoxystyrene, 2-hydroxymethylstyrene, 4-ethylstyrene, 4-ethoxystyrene, 3,4-dimethylstytene, 2-chlorostyrene, 3-chlorostyrene, 4-chloro-3-methylstyrene, 3-tert-butylstyrene, 2,4-dichlorostyrene, 2,6-dichlorostyrene and 1-vinylnaphthalene;

an unsaturated nitrile such as acrylonitrile or methacrylonitrile, an N-substituted maleimide such as N-ethylmaleimide, N-isopropylmealeide, N-n-butylmaleimide, N-isobutylmaleimide, N-tert-butylmaleimide, N-n-octylmalemide, N-cyclohexylmalemide, N-benzylmaleimide and N-phenylmaleimide, an unsaturated dicarboxylic acid anhydride such as maleic anhydride, iraconic anhydride, citraconic anhydride or tetrahydrophthalic anhydride, acrylic or methacrylic acid, a polyol acrylate or methacrylate such as the diacrylates and dimethacrylates of ethylene glycol, propylene glycol, 1,3-butanediol, 1,4-butanediol, 1,6-hexanediol, neopentylglycol, 1,4-cyclohexanediol, 1,4-cyclohexanedimethanol, 2,2,4-trimethyl-1,3-pentanediol, 2-ethyl-2-methyl-1,3-propanediol, 2,2-diethyl-1,3-propanediol, diethylene glycol, dipropylene glycol, triethylene glycol, tripropylene glycol, tetraethylene glycol, tetrapropylene glycol, trimethylolethane, trimethylolpropane, glycerol, pentaerythritol, the triacrylates and trimethacrylates of trimethylolethane, trimethylolpropane, glycerol and pentaerythritol, pentaerythritol tetraacrylates and tetramethacrylates, dipentaerythritol di(meth)acrylates to hexa(meth)acrylates, poly(meth)acrylates of mono- or polyethoxylated or mono- or polypropoxylated polyols such as triethoxylated trimethylolpropane and tripropoxylated trimethylolpropane triacrylate and trimethacrylate; tripropoxylated glycerol triacrylate and trimethacrylate; and tetraethoxylated pentaerythritol triacrylate, trimethacrylate, tetraacrylate and tetramethacrylate, an epoxidised acrylate or methacrylate chosen from 2-epoxyethylbicyclo[2.2.1]hept-5(6)-yl (meth)-acrylate, epoxydicyclopentyloxyethyl acrylate, and those of formula:

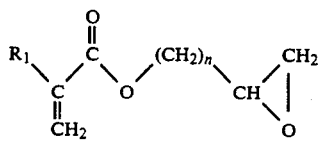

in which $R_1$ is chosen from the hydrogen atom and the methyl radical, and n is an integer ranging from 1 to 16, those of formula:

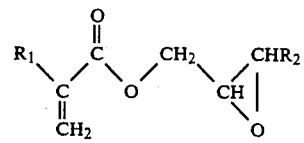

in which $R_1$ is chosen from the hydrogen atom and the methyl radical, and $R_2$ is chosen from alkyl radicals containing from 1 to 12 carbon atoms and aryl radicals containing from 6 to 12 carbon atoms, and those of formulae:

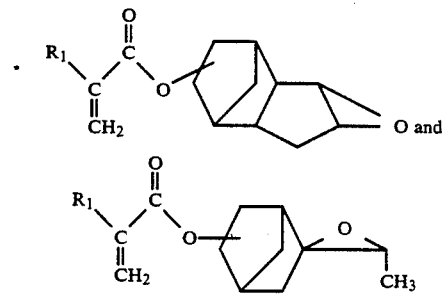

in which $R_1$ is chosen from the hydrogen atom and the methyl radical, an acrylamide or methacrylamide or a dialkylaminoalkyl acrylate or methacrylate, and their quaternary salts, 2-(2-norbornyloxy)ethyl and 2-(2-dimethanodecahydronaphthyloxy)ethyl acrylate and methacrylate, and acrylic and methacrylic oxazolidones chosen from those of formula:

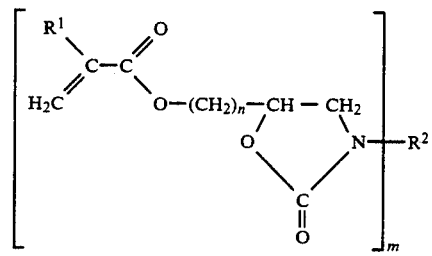

and those of formula:

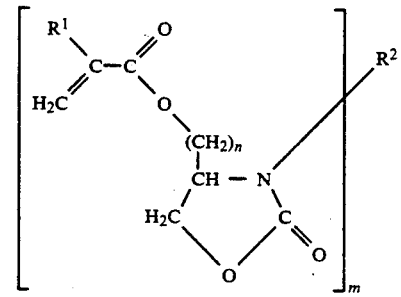

in which formulae:

$R^1$ is chosen from the hydrogen atom and the methyl radical, n is an integer ranging from 1 to 12, m is an integer ranging from 1 to 3, and $R^2$ is a branched or cyclic linear alkyl or aromatic hydrocarbon radical containing from 5 to 12 carbon atoms, it being possible for the said oxazolidones to be obtained by reaction, between 30° C. and 90° C., of a compound carrying a (meth)acrylic functional group with a compound carrying at least one isocyanate functional group, acrylic and methacrylic compounds chosen from those of formula:

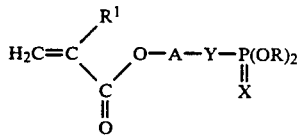

in which:

$R^1$ is chosen from the hydrogen atom and the methyl radical,

A is chosen from the radicals $(CH_2)_n$ in which n is an integer from 2 to 12 and the radical $-(CH_2CH_2O)_d-CH_2CH_2-$, d being an integer ranging from 1 to 20, X is chosen from sulphur and oxygen atoms, Y is chosen from sulphur and oxygen atoms, with the condition that X is a sulphur atom and Y is an oxygen atom when A is the radical $-(CH_2CH_2O)_d-CH_2CH_2-$, and R is chosen from alkyl radicals containing from 1 to 20 carbon atoms and $-(CH_2)_pSR^3$ groups in which p is an integer ranging from 3 to 12 and $R^3$ is an alkyl radical containing from 1 to 20 carbon atoms, those of formula:

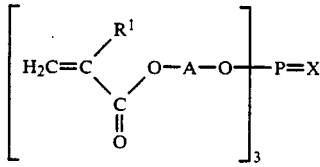

in which:

$R^1$ is chosen from the hydrogen atom and the methyl radical,

A is chosen from the radicals $(CH_2)_n$ in which n is an integer from 2 to 12 and the radical $-(CH_2CH_2O)_d-CH_2CH_2-$, d being an integer ranging from 1 to 20, and X is chosen from sulphur and oxygen atoms, and those of formula:

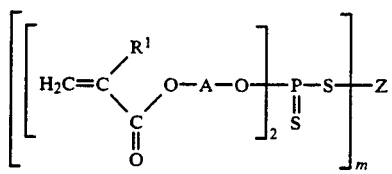

in which:

$R^1$ is chosen from the hydrogen atom and the methyl radical,

A is chosen from the radicals $(CH_2)_n$ in which n is an integer from 2 to 12, m is an integer from 1 to 3, and Z is chosen from the hydrogen atom, the radicals $R^2QH$, $R^2$ being an alkyl radical containing from 2 to 12 carbon atoms and Q being chosen from oxygen and sulphur atoms and the atoms of metals of groups IA, IIA, IIIA, IB, IIB, VIB, VIIB and VIII of the Periodic Classification, with the condition that Z is chosen from the hydrogen atom and the radicals $R^2OH$ when m=1 and that m is the valency of Z when Z is a metal. Such compounds can be prepared by reaction of an acrylic or methacrylic compound of formula:

in which $R^1$ A and Y have the same meanings as in the formula (I), with a pentavalent phosphorus compound, it being possible for the latter to be, for example, a compound of formula $PXT_3$ in which X has the same meaning as in formula (II) and T denotes a halogen atom, or else a phosphorus compound of formula:

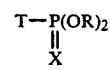

in which R and X have the same meanings as in formula (I) and T denotes a halogen atom or else the pentasulphide $P_2S_5$, and generally any ethylenically unsaturated monomers capable of being copolymerised by a radical process under the effect of a free-radical generator such as microwaves, beta, gamma or ultraviolet radiation or a chemical initiator such as persulphate, peroxide, hydroperoxide or diazo compound.

Thus, a third subject of the present invention consists of a polymer comprising in its chain at least one unit derived from an acrylate of formula (I), (II) or (III) with the condition that Y may also denote 1,4-phenylene when R denotes methyl and, if appropriate, at least one unit derived from another ethylenically unsaturated monomer such as described above. In the case of copolymers, the polymerisation conditions will be chosen to be as close as possible to those usually employed for the polymerisation of the ethylenically unsaturated monomer, namely, for example:

a temperature of 140° C. to 300° C. and a pressure approximately from 1000 to 3000 bars when this comonomer is ethylene, a temperature approximately from 30° C. to 90° C. when this comonomer is an acrylic or methacrylic compound, a temperature approximately from 80° C. to 200° C. when this comonomer is a vinylaromatic hydrocarbon.

The polymers of this invention can be used in the same conventional manner as other acrylic and methacrylic polymers, e.g., formed into molded, cast, and extruded articles, coating materials, etc.

(In the above description and throughout the specification and claims, the numerical range of "from x to y", x and y being integers, is intended to include both x and y.)

The entire disclosure of all applications, patents, and publications, cited above and below, and of corresponding French Application 90 08108, filed Jun. 27, 1990, are hereby incorporated by reference.

EXAMPLES

The following examples are given by way of illustration of the present invention, no limitation being employed.

EXAMPLES 1 TO 25

26.8 g (0.2 mol) of terephthalaldehyde, x mol of diazabicyclo[2.2.2]octane, y mol of methyl acrylate and z ml of solvent are introduced successively into a glass round bottom flask of 3 l capacity fitted with a condenser. The mixture is stirred at the temperature T (expressed in degrees Celsius) for the period t (expressed in hours). The percentages M of monoacrylate and D of diacrylate which are present in the reaction mixture at the end of the time t or determined by gas phase chromatography and reported in Table I below at the same time as the reaction parameters. 200 ml of methyl chloride and 120 ml of 1 N hydrochloric acid are then added to the mixture. The aqueous phase is extracted once with 40 ml of methylene chloride. The organic phase is washed twice with 80 ml of water and is then dried over magnesium sulphate. After evaporation of the solvent the mono- or diacrylate formed is purified on a silica column, the eluent being a mixture containing 35% of ethyl acetate and 65% of petroleum ether. The monoacrylate (methyl 3-(4-carboxaldehydephenyl)-3-hydroxy-2-methylenepropanoate) is a colourless liquid and can be isolated in a 94% yield, for example in test 10. The diacrylate (1,4-di(methyl 3-hydroxy-2-methylenecarboxylate)benzene) is a white solid and can be isolated in a 90% yield, for example in test 21. Both were identified by the following techniques:

proton nuclear magnetic resonance employing a JEOL PMX 60SI spectrometer: the spectra obtained include chemical shifts a) 9.8 (s,1H) 7.3-7.8 (m,4H) 6.2 (m, 1H) 5.9 (m, 1H) 5.5 (m, 1H) 3.9 (m, 1H,OH) 3.6 (s,3H) in ppm in the case of the monoacrylate.

b) 7.3 (s,4H) 6.3 (m,.2H) 5.8 (m,2H) 5.5 (m,2H) 3.7 (s,6H) 2.9 (m,2H,OH) in ppm in the case of the diacrylate.

infrared spectrophotometry employing a Perkin Elmer 841 spectrometer: the spectra obtained include characteristic bands at:

c) 3477, 1724, 1703, 1631, 1609, 1579, 1439 cm$^1$ in the case of the monoacrylate.

d) 3459, 1724, 1631 and 1439 cm$^1$ in the case of the diacrylate.

carbon-13 nuclear magnetic spectroscopy: chemical shifts at 191.9 ppm, 165.9 ppm, 148.3 ppm, 141.3 ppm, 135.2 ppm, 129.4 ppm, 127.0 ppm, 126.0 ppm, 71.8 ppm and 51.6 ppm in the case of the monoacrylate; at 166.7 ppm, 141.8 ppm, 140.3 ppm, 127.1 ppm, 127.0 ppm, 126.2 ppm, 73.0 ppm and 52.0 ppm in the case of the diacrylate.

TABLE I

| Example | x | y | z | Solvent | T | t | M | D |
|---|---|---|---|---|---|---|---|---|
| 1 | 0.1 | 1.0 | 50 | THF | 20 | 8 | 98 | 2 |
| 2 | 0.1 | 1.0 | 50 | THF | 20 | 96 | 46 | 54 |
| 3 | 0.1 | 1.0 | 50 | THF | 20 | 192 | 35 | 65 |
| 4 | 0.1 | 1.0 | 50 | THF | 20 | 288 | 19 | 81 |
| 5 | 0.1 | 1.0 | 50 | CH$_2$Cl$_2$ | 20 | 8 | 95 | 5 |
| 6 | 0.1 | 1.0 | 50 | CH$_2$Cl$_2$ | 20 | 96 | 35 | 65 |
| 7 | 0.1 | 1.0 | 50 | CH$_2$Cl$_2$ | 20 | 192 | 26 | 74 |
| 8 | 0.1 | 1.0 | 50 | CH$_2$Cl$_2$ | 20 | 240 | 23 | 77 |

TABLE I-continued

| Example | x | y | z | Solvent | T | t | M | D |
|---|---|---|---|---|---|---|---|---|
| 9 | 0.1 | 1.0 | 50 | CHCl$_3$ | 20 | 96 | 97 | 3 |
| 10 | 0.1 | 0.4 | 0 | — | 20 | 2.5 | 96 | 4 |
| 11 | 0.1 | 0.4 | 10 | THF | 20 | 3 | 94 | 2 |
| 12 | 0.1 | 0.4 | 44 | THF | 20 | 3 | 94 | 3 |
| 13 | 0.1 | 0.4 | 44 | THF | 20 | 24 | 82 | 18 |
| 14 | 0.1 | 0.4 | 44 | THF | 20 | 96 | 50 | 50 |
| 15 | 0.1 | 0.4 | 164 | THF | 20 | 96 | 98 | 2 |
| 16 | 0.4 | 2.0 | 20 | THF | 20 | 96 | 30 | 70 |
| 17 | 0.4 | 2.0 | 20 | THF | 20 | 240 | 9 | 91 |
| 18 | 0.1 | 0.2 | 50 | THF | 20 | 8 | 80 | 0 |
| 19 | 0.1 | 0.2 | 50 | THF | 20 | 24 | 96 | 2 |
| 20 | 0.1 | 1.0 | 0 | — | 20 | 2 | 85 | 4 |
| 21 | 0.2 | 2.0 | 0 | — | 20 | 96 | 2 | 96 |
| 22 | 0.4 | 2.0 | 20 | THF | 45 | 72 | 19 | 81 |
| 23 | 0.4 | 2.0 | 20 | THF | 45 | 192 | 4 | 96 |
| 24 | 0.4 | 2.0 | 20 | THF | 55 | 24 | 61 | 39 |
| 25 | 0.4 | 2.0 | 20 | THF | 55 | 72 | 18 | 82 |
| 26* | 0.1 | 1.0 | 0 | — | 20 | 0.8 | 95 | 5 |

*test carried out in the presence of lithium chloride.
THF = tetrahydrofuran.

EXAMPLE 26

The experimental procedure of Example 20 is reproduced with the following two exceptions:

0.8 g (0.02 mol) of lithium chloride is added to the reaction mixture, the reaction is interrupted after 50 minutes.

Analysis of the mixture at the end of the reaction makes it possible to determine the percentages M of monoacrylate and D of diacrylate which are shown in the table.

EXAMPLES 27 to 35

26.8 g (0.2 mol) of isophthalaldehyde, x mol of diazabicyclo[2.2.2]octane, y mol of methyl acrylate, z ml of solvent and, if appropriate, q mol of lithium chloride are introduced successively into a glass round bottom flask of 3 l capacity. The mixture is stirred at a temperature of 25° C. for the period t, expressed in hours. The mixture is then treated as in Examples 1 to 25. The percentages M of monoacrylate and D of diacrylate which are present in the reaction mixture at the end of the time t are determined by gas chromatography and reported in Table II below at the same time as the reaction parameters. The monoacrylate (methyl 3-(3-carboxaldehydephenyl)-3-hydroxy-2-methylenepropanoate) and the diacrylate (1,3-di(methyl 3-hydroxy-2-methylenecarboxylate)-benzene) are colourless liquids. They can be isolated in tests 28 and 36 in yields of 88% and 96% respectively. Both were identified by the same techniques as those mentioned in Examples 1 to 25 and exhibit the following 30 spectral characteristics:

proton nuclear magnetic resonance:

a) 9.7 (s,1H) 7.3-7.8 (m,4H) 6.2 (m, 1H) 5.8 (m, 1H) 5.5 (m, 1H) 4.0 (m, 1H,OH) 3.6 (s,3H) in ppm in the case of the monoacrylate;

b) 7.3 (m,4H) 6.3 (m,2H) 5.8 (m,2H) 5.5 (m,2H) 3.7 (s,6H) 3.3 (m,2H,OH) in ppm in the case of the diacrylate;

infrared spectrophotometry:

c) absorption bands at 3471 cm$^{-1}$, 1723 cm$^{-1}$, 1701 cm$^{-1}$, 1630 cm$^{-1}$, 1603 cm$^{-1}$, 1587 cm$^{-1}$ and 1441 cm$^{-1}$ in the case of the monoacrylate;

d) absorption bands at 3458 cm$^{-1}$, 1723 cm$^{-1}$, 1632 cm$^{-1}$ and 1441 cm$^{-1}$ in the case of the diacrylate carbon-13 nuclear magnetic spectroscopy:

chemical shifts at 192.1 ppm, 165.3 ppm, 142.6 ppm, 141.4 ppm, 135.8 ppm, 132.6 ppm, 128.5 ppm, 128.4 ppm, 127.7 ppm, 125.6 ppm, 71.3 ppm and 51.4 ppm in the case of the monoacrylate (FIG. 1c); at 166.1 ppm, 141.8 ppm, 141.2 ppm, 127.8 ppm, 125.75 ppm, 125.2 ppm, 124.9 ppm, 71.6 ppm and 51.3 ppm in the case of the diacrylate.

TABLE II

| Example | x | y | z | q | Solvent | t | M | D |
|---|---|---|---|---|---|---|---|---|
| 27 | 0.1 | 1.0 | 0 | 0 | — | 3 | 68 | 1 |
| 28 | 0.1 | 1.0 | 0 | 0 | — | 5 | 85 | 10 |
| 29 | 0.1 | 1.0 | 0 | 0 | — | 24 | 30 | 70 |
| 30 | 0.1 | 1.0 | 0 | 0.02 | — | 2 | 82 | 18 |
| 31 | 0.1 | 1.0 | 0 | 0.02 | — | 24 | 14 | 86 |
| 32 | 0.1 | 1.0 | ·0 | 0.02 | — | 48 | 8 | 92 |
| 33 | 0.2 | 0.4 | 50 | 0 | THF | 3 | 37 | 0 |
| 34 | 0.2 | 0.4 | 50 | 0 | THF | 12 | 86 | 3 |
| 35 | 0.2 | 0.4 | 50 | 0.02 | THF | 3 | 90 | 3 |
| 36 | 0.2 | 2.0 | 0 | 0 | — | 72 | 2 | 96 |

EXAMPLE 37

26.8 g (0.2 mol) of ortho-phthalaldehyde, 11.2 g (0.1 mol) of diazabicyclo[2.2.2]octane, 90 nil (1 mol) of methyl acrylate and 50 ml of tetrahydrofuran are introduced successively into a glass round bottom flask of 3 1 capacity. The mixture is stirred at 25° C. for 4 hours and is then treated as in Examples 1 to 25. Analysis by gas phase chromatography shows the formation, in an isolated yield of 86%, of a compound identified as that of formula

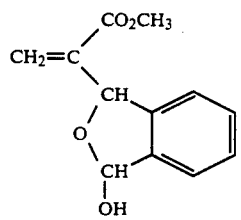

by infrared spectrophotometry by means of a Perkin-Elmer 841 spectrometer. The spectrum obtained includes characteristic bands at 3459 cm$^{-1}$, 1721 cm$^{-1}$, 1631 cm$^{-1}$, 1463 cm$^{-1}$ and 1439 cm$^{-1}$.

EXAMPLE 38

0.2 mol of 50% aqueous glutaraldehyde, 1 mol of methyl acrylate, 0.1 mol of diazabicyclo[2.2.2]octane and 50 ml of dichloromethane are introduced successively into a glass round bottom flask 3 1 in capacity. The mixture is stirred at 25° C. for 144 hours and is then treated as in Examples 1 to 25. Analysis by gas phase chromatography shows the formation, in a 30% yield, of a compound identified as that of formula

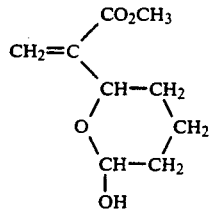

by infrared spectrophotometry by means of a Perkin-Elmer 841 spectrometer. The spectrum obtained includes characteristic bands at 3435, 1721 and 1632 cm$^{-1}$;

by carbon-13 nuclear magnetic resonance:
chemical shifts at 166.0 ppm, 165.9 ppm, 141.5 ppm, 140.5 ppm, 124.4 ppm, 124.0 ppm, 96.3 ppm, 91.5 ppm, 73.1 ppm, 65.9 ppm, 51.3 ppm, 31.7 ppm, 31.1 ppm, 30.4 ppm, 29.2 ppm, 21.8 ppm, 17.1 ppm and 15.6 ppm;

by proton nuclear magnetic resonance: chemical shifts at 6.25 ppm (m,1H), 6.25 ppm (m,O,5H), 6.05 ppm (m,O,5H), 5.45 to 4.1 (m2H+10H), 3.75 ppm (s3H) and 2.3 to 0.8 ppm (m6H).

EXAMPLE 39

0.2 mol of glutaraldehyde (obtained by distillation from 50% aqueous glutaraldehyde) and 1 mol of methyl acrylate, 0.1 mol of diazabicyclo[2.2.2]octane are introduced successively into a glass round bottom flask of 3 1 capacity. The mixture is stirred at 25° C. for 72 hours and is then treated as in Examples 1 to 25. The isolated yield of product:

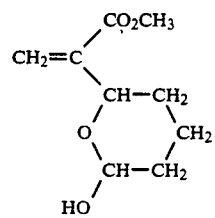

is 85%.

EXAMPLE 40

0.2 mol of thiophene-2,5-dicarboxaldehyde, 0.4 mol of methyl acrylate, 0.2 mol of diazabicyclo[2.2.2]octane and 50 ml of dichloromethane are introduced successively into a glass round bottom flask of 3 1 capacity. The mixture is stirred at 25° C. for 105 minutes and is then treated as in Examples 1 to 25. Analysis by gas phase chromatography shows the formation, in an isolated yield of 67%, of a compound identified as that of formula

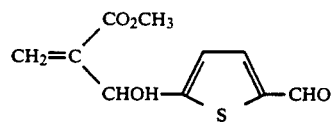

by the following techniques
infrared spectrophotometry: the spectrum obtained shows characteristic bands at 3462 cm$^{-1}$, 1718 cm$^{-1}$, 1670 cm$^{-1}$ and 1456 cm$^{-1}$:

carbon-13 nuclear magnetic resonance:
chemical shifts at 183.3 ppm, 165.9 ppm, 157.5 ppm, 142.3 ppm, 140.6 ppm, 136.9 ppm, 126.8 ppm, 125.6 ppm, 68.8 ppm and 52.0 ppm;

proton nuclear magnetic resonance:
chemical shifts at 9.8 ppm (s,1H), 7.6 ppm (d,1H), 7.1 ppm (d,1H), 6.4 ppm (m,1H), 6.1 ppm (m,1H), 5.8 ppm (m,1H), 4.2 ppm (m,1H,OH) and 3.7 ppm (s,3H).

EXAMPLE 41

0.2 mol of thiophene-2,5-dicarboxaldehyde, 2 mol of methyl acrylate and 0.2 mol of diazabicyclo[2.2.2]-octane are introduced successively into a glass round bottom flask of 3 1 capacity. The mixture is stirred at 25° C. for 46 hours and is then treated as in Examples 1 to 25. Analysis by gas phase chromatography shows the formation, in an isolated yield of 67%, of the diacrylate of formula:

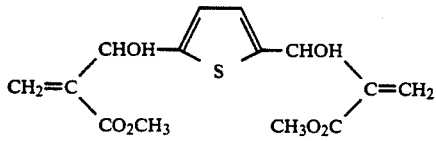

The latter was identified by:
  infrafred spectrophotometry: the spectrum obtained shows characteristic bands at 3460 cm$^{-1}$, 1709 cm$^{-1}$, 1632 cm$^{-1}$ and 1439 cm$^{-1}$;
  proton nuclear magnetic resonance:
    chemical shifts at 6.7 ppm (s,2H), 6.3 ppm (m,2H), 6.0 ppm (m,2H), 5.7 ppm (m,2H), 3.7 ppm (s,6H) and 3.5 ppm (m,2H,OH);
  carbon-13 nuclear magnetic resonance:
    chemical shifts at 166.2 ppm, 145.3 ppm, 141.1 ppm, 125.8 ppm, 124.4 ppm, 66.6 ppm and 51.6 ppm. EXAMPLE 42

0.2 mol of 4,4'-biformyldiphenyl, 1 mol of methyl acrylate and 0.2 mol of diazabicyclo[2.2.2]octane and 150 ml of tetrahydrofuran are introduced successively into a glass round bottom flask 3 1 in capacity. The mixture is stirred at 25° C. for 20 days and is then treated as in Examples 1 to 25. A 56% yield is obtained of the compound identified as that of formula:

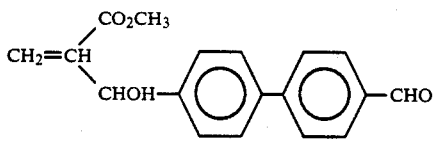

by the following techniques:
  infrared spectroscopy: the spectrum obtained shows characteristic bands at 3474 cm$^{-1}$, 1722 cm$^{-1}$, 1702 cm$^{-1}$ and 1631 cm$^{-1}$;
  proton nuclear magnetic resonance:
    chemical shifts at 9.9 ppm (s,1H), 7.85 to 7.55 ppm (m,8H), 6.37 ppm (m,1H), 5.95 ppm (m,1H), 5.65 ppm (m,1H), 3.7 ppm (s,3H) and 3.4 ppm (m, 1H,OH);
  carbon-13 nuclear magnetic resonance:
    chemical shifts at 191.8 ppm, 166.25 ppm, 146.3 ppm, 141.8 ppm, 138.5 ppm, 134.7 ppm, 129.1 ppm, 127.1 ppm, 127.0 ppm, 125.2 ppm, 72.0 ppm and 51.6 ppm.

EXAMPLE 43

0.2 mol of 4,4'-biformyldiphenyl, 2 mol of methyl acrylate and 0.4 mol of diazabicyclo[2.2.2]octane are introduced successively into a glass round bottom flask 3 1 in capacity. The mixture is stirred at 25° C. for 168 hours and is then treated as in Examples 1 to 25. Analysis by gas phase chromatography shows the formation, in an isolated yield of 86%, of the diacrylate of formula:

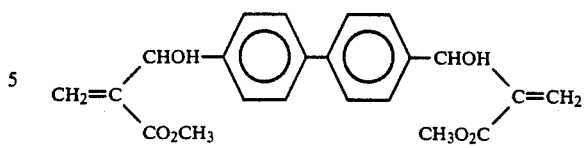

The latter was identified by:
  infrared spectrophotometry: the spectrum obtained shows characteristic bands at 3466 cm$^{-1}$, 1724 cm$^{-1}$, 1702 cm$^{-1}$, 1629 cm$^{-1}$, 1494 cm$^{-1}$ and 1437 cm$^{-1}$;
  proton nuclear magnetic resonance:
    chemical shifts at 7.6 ppm (m,8H), 6.4 ppm (m,2H), 5.9 ppm (m,2H), 5.6 ppm (m,2H) and 3.8 ppm (s,6H);
  carbon-13 nuclear magnetic resonance:
    chemical shifts at 166.5 ppm, 141.8 ppm, 140.8 ppm, 126.6 ppm, 125.6 ppm, 72.3 ppm and 51.7 ppm.

EXAMPLE 44

0.2 mol of furan-2,5-dicarboxaldehyde, 1 mol of methyl acrylate, 0.2 mol of diazabicyclo[2.2.2]octane and 30 ml of tetrahydrofuran are introduced successively into a glass round bottom flask 3 1 in capacity. The mixture is stirred at 20° C. for 4 hours and is then treated as in Examples 1 to 25. Analysis by gas phase chromatography shows the formation, in an isolated yield of 50%, of the monoacrylate of formula:

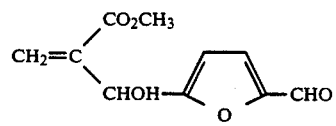

The latter was identified by:
  infrared spectroscopy: the spectrum obtained shows characteristic bands at 3454 cm$^{-1}$, 1725 cm$^{-1}$, 1705 cm$^{-1}$, 1678 cm$^{-1}$ and 1582 cm$^{-1}$;
  proton nuclear magnetic resonance:
    chemical shifts at 9.8 ppm (s,1H), 7.3 ppm (d, 1H,J=4 Hz), 6.6 ppm (d, 1H,J=4 Hz), 6.5 ppm (m, 1H), 6.2 ppm (m, 1H), 5.8 ppm (m, 1H), 4.3 ppm (m, 1H,OH) and 3.8 ppm (s,3H);
  carbon-13 nuclear magnetic resonance:
    chemical shifts at 177.7 ppm, 165.6 ppm, 161.1 ppm, 151.6 ppm, 139.4 ppm, 127.2 ppm, 109.6 ppm, 65.7 ppm and 51.7 ppm.

EXAMPLE 45

0.2 mol of furan-2,5-dicarboxaldehyde, 2 mol of methyl acrylate and 0.4 mol of diazabicyclo[2.2.2]octane are introduced successively into a glass round bottom flask 3 1 in capacity. The mixture is stirred at 20° C. for hours and is then treated as in Examples 1 to 25. Analysis by gas phase chromatography shows the formation, in an isolated yield of 60%, of the diacrylate of formula:

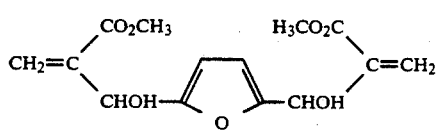

The latter was identified by:

infrared spectroscopy: the spectrum obtained shows characteristic bands at 3457 cm$^{-1}$, 1723 cm$^{-1}$ and 1635 cm$^{-1}$;

proton nuclear magnetic resonance:

chemical shifts at 6.4 ppm (m,2H), 6.2 ppm (s,2H), 6.0 ppm (m,2H), 5.6 ppm (m,2H), 3.8 ppm (s,6H) and 4-3.5 ppm (m,2H,OH);

carbon-13 nuclear magnetic resonance:

chemical shifts at 166.0 ppm, 153.7 ppm, 139.3 ppm, 126.1 ppm, 107.6 ppm, 65.3 ppm and 51.6 ppm.

EXAMPLE 46

0.2 mol of 3,3'-biformyldiphenyl, 1 mol of methyl acrylate, 0.2 mol of diazabicyclo[2.2.2]octane and 150 ml of tetrahydrofuran are introduced successively into a glass round bottom flask 3 l in capacity. The mixture is stirred at 20° C. for 192 hours and is then treated as in Examples 1 to 25. Analysis by gas phase chromatography shows the formation, in an isolated yield of 56%, of the monoacrylate of formula:

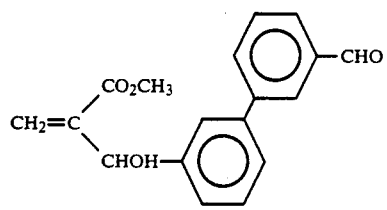

The latter was identified by:

infrared spectroscopy: the spectrum obtained shows characteristic bands at 3489 cm$^{-1}$, 1724 cm$^{-1}$, 1704 cm$^{-1}$, 1631 cm$^{-1}$, 1602 cm$^{-1}$, 1581 cm$^{-1}$, 1474 cm$^{-1}$ and 1441 cm$^{-1}$;

proton nuclear magnetic resonance:

chemical shifts at 10.1 ppm (s,1H), 8.2 to 7.3 ppm (m,8H), 6.3 ppm (m, 1H), 5.9 ppm (m, 1H), 5.75 to 5.5 ppm (m, 1H), 3.7 ppm (s,3H) and 3.6 to 3.4 ppm (m, 1H,OH);

carbon-13 nuclear magnetic resonance:

chemical shifts at 192.2 ppm, 166.2 ppm, 142.2 ppm, 141.9 ppm, 141.3 ppm, 139.1 ppm, 136.3 ppm, 132.6 ppm, 129.0 ppm, 128.6 ppm, 128.2 ppm, 127.7 ppm, 126.1 ppm, 126.0 ppm, 125.4 ppm, 125.1 ppm, 72.1 ppm and 65.3 ppm.

EXAMPLE 47

0.2 mol of 3,3'-biformyldiphenyl, 2 mol of methyl acrylate and 0.4 mol of diazabicyclo[2.2.2]octane are introduced successively into a glass round bottom flask 1 l in capacity. The mixture is stirred at 20° C. for hours and is then treated as in Examples 1 to 25. Analysis by gas phase chromatography shows the formation, in an isolated yield of 94%, of the diacrylate of formula:

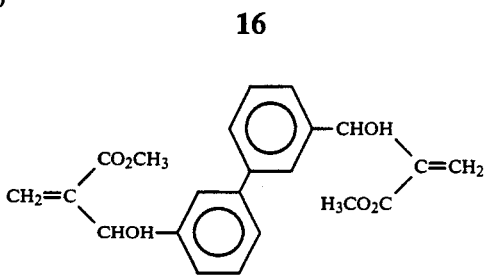

The latter was identified by:

infrared spectroscopy: the spectrum obtained shows characteristic bands at 3471 cm$^{-1}$, 1724 cm$^{-1}$, 1632 cm$^{-1}$, 1604 cm$^{-1}$, 1583 cm$^{-1}$, 1475 cm$^{-1}$ and 1440 cm$^{-1}$;

proton nuclear magnetic resonance:

chemical shifts at 7.8 to 7.3 ppm (m,8H), 6.4 ppm (m,2H), 5.9 ppm (m,2H), 5.6 ppm (m,2H), 3.7 ppm (s,6H) and 3.5 ppm (m,2H,OH);

carbon-13 nuclear magnetic resonance:

chemical shifts at 166.5 ppm, 141.9 ppm, 141.8 ppm, 140.8 ppm, 128.6 ppm, 126.4 ppm, 125.8 ppm, 125.5 ppm, 125.3 ppm, 72.3 ppm and 51.6 ppm.

Polymers and copolymers can be made from any and all of the monomers produced in the above examples.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. An acrylates the formula

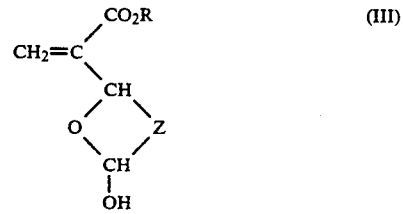

in which:

R is a radical chosen from alkyl radicals containing from 1 to 12 carbon atoms, cycloalkyl radicals containing from 5 to 12 carbon atoms, and aryl, arylalkyl and alkylaryl radicals, Z is a hydrocarbon radical containing at least two carbon atoms forming with the oxygen and the two adjacent carbons a ring containing from 4 to 8 members.

2. An acrylates according to claim 1, wherein Z is chosen from the radicals (CH$_2$)$_2$ and (CH$_2$)$_3$ and the phenylene radical C$_6$H$_4$.

3. An acrylate according to claim 1, wherein Z is (CH$_2$)$_2$.

4. An acrylate according to claim 1, wherein Z is (CH$_2$)$_3$.

5. An acrylate according to claim 1, wherein Z is phenylene.

6. An acrylate according to claim 3 wherein R is methyl.

7. An acrylate according to claim 4, wherein R is methyl.

8. An acrylate according to claim 5, wherein R is methyl.

* * * * *

UNITED STATES PATENT AND TRADEMARK OFFICE
CERTIFICATE OF CORRECTION

PATENT NO. : 5,332,836
DATED : July 26, 1994
INVENTOR(S) : Marie-Christine BERTHE et al.

It is certified that error appears in the above-indentified patent and that said Letters Patent is hereby corrected as shown below:

Claim 1, column 16, line 35: Change "acrylates" to read --acrylate--.

Claim 1, column 16, line 35: After "acrylate" insert --of--.

Claim 2, Column 16, line 54: Change "acrylates" to read --acrylate--.

Signed and Sealed this

Thirteenth Day of December, 1994

Attest:

BRUCE LEHMAN

Attesting Officer      Commissioner of Patents and Trademarks